United States Patent
Saruwatari et al.

(10) Patent No.: US 11,892,388 B2
(45) Date of Patent: Feb. 6, 2024

(54) SIMULATION DEVICE, SIMULATION METHOD, AND PROGRAM

(71) Applicants: SUMITOMO METAL MINING CO., LTD., Tokyo (JP); University Public Corporation Osaka, Osaka (JP)

(72) Inventors: Motoaki Saruwatari, Ehime (JP); Hideya Nakamura, Osaka (JP)

(73) Assignees: SUMITOMO METAL MINING CO., LTD., Tokyo (JP); University Public Corporation Osaka, Osaka (JP)

(*) Notice: Subject to any disclaimer, the term of this patent is extended or adjusted under 35 U.S.C. 154(b) by 0 days.

(21) Appl. No.: 18/058,808

(22) Filed: Nov. 25, 2022

(65) Prior Publication Data
US 2023/0091287 A1 Mar. 23, 2023

Related U.S. Application Data

(63) Continuation-in-part of application No. PCT/JP2021/020745, filed on May 31, 2021.

(30) Foreign Application Priority Data

Jun. 1, 2020 (JP) .................................. 2020-095620
Sep. 28, 2020 (JP) .................................. 2020-162719

(51) Int. Cl.
*G01N 15/10* (2006.01)
*G01N 15/14* (2006.01)
(Continued)

(52) U.S. Cl.
CPC ..... *G01N 15/1012* (2013.01); *G01N 15/1425* (2013.01); *G16C 20/30* (2019.02);
(Continued)

(58) Field of Classification Search
CPC . G01N 15/1012; G01N 15/1425; G16C 20/30
(Continued)

(56) References Cited

U.S. PATENT DOCUMENTS 8,234,074 B2 * 7/2012 Lopez .................... G16C 10/00
702/19
8,781,799 B2 * 7/2014 Ichishima .............. G16C 10/00
703/2
(Continued)

FOREIGN PATENT DOCUMENTS

| CN | 102548926 | 7/2012 |
| CN | 104395071 | 3/2015 |

(Continued)

OTHER PUBLICATIONS

Zhang et al. ("A DEM study on the effective thermal conductivity of granular assemblies", Powder Technology 205 (2011) 172-183) (Year: 2011).*

(Continued)

*Primary Examiner* — Iftekhar A Khan
(74) *Attorney, Agent, or Firm* — IPUSA, PLLC

(57) ABSTRACT

A simulation device for analyzing behavior of a granular material that includes a plurality of particles includes a first parameter acquisition unit that acquires a first parameter including a parameter relating to the granular material, a second parameter calculation unit that calculates a second parameter, when a particle group including the plurality of particles is coarsely viewed as a single coarse-view particle, the second parameter relating to the coarse-view particle, and a coarse-view particle behavior analysis unit that analyzes a behavior of the coarse-view particle based on the first parameter and the second parameter. The second parameter calculation unit calculates the second parameter by solving a characteristic equation that uses a relationship between an
(Continued)

elastic energy of the particle group and an elastic energy of the coarse-view particle.

7 Claims, 12 Drawing Sheets

(51) Int. Cl.
*G16C 20/30* (2019.01)
*G01N 15/00* (2006.01)

(52) U.S. Cl.
CPC ............... *G01N 2015/0003* (2013.01); *G01N 2015/1025* (2013.01)

(58) Field of Classification Search
USPC .................................................. 703/6
See application file for complete search history.

(56) References Cited

U.S. PATENT DOCUMENTS

| | | | | |
|---|---|---|---|---|
| 9,183,676 B2* | 11/2015 | McCulloch | ........... | G06T 19/006 |
| 11,288,419 B2* | 3/2022 | Ishihara | ................ | G06F 30/25 |
| 2006/0235659 A1* | 10/2006 | Stam | ................ | G06T 13/20 |
| | | | | 703/2 |
| 2007/0239414 A1* | 10/2007 | Song | ................ | G06F 30/23 |
| | | | | 703/9 |
| 2007/0244676 A1* | 10/2007 | Shang | ................ | G06F 30/23 |
| | | | | 703/2 |
| 2010/0094608 A1* | 4/2010 | Oh | ................ | G06F 30/20 |
| | | | | 703/9 |
| 2010/0185420 A1* | 7/2010 | Ding | ................ | G06F 30/23 |
| | | | | 703/2 |
| 2012/0150496 A1* | 6/2012 | Yu | ................ | G06F 30/23 |
| | | | | 703/2 |
| 2012/0183756 A1* | 7/2012 | Higuchi | ........... | B32B 17/10798 |
| | | | | 156/306.9 |
| 2014/0303945 A1* | 10/2014 | Ueno | ................ | G06F 30/20 |
| | | | | 703/2 |
| 2014/0358505 A1* | 12/2014 | Hashash | ................ | G06F 30/23 |
| | | | | 703/2 |
| 2015/0174861 A1* | 6/2015 | Hasegawa | ......... | B32B 17/10752 |
| | | | | 428/339 |
| 2015/0186565 A1* | 7/2015 | Stomakhin | ................ | G06F 30/20 |
| | | | | 703/6 |
| 2015/0187116 A1* | 7/2015 | Stomakhin | ................ | G06T 13/60 |
| | | | | 345/419 |
| 2015/0325028 A1* | 11/2015 | Kim | ................ | G06T 7/20 |
| | | | | 345/419 |
| 2016/0055279 A1* | 2/2016 | Ichishima | ................ | G06F 30/20 |
| | | | | 703/2 |
| 2017/0061048 A1* | 3/2017 | Grace | ................ | G06F 30/23 |
| 2018/0023988 A1* | 1/2018 | Ogasawara | ................ | B29C 45/77 |
| | | | | 702/47 |
| 2018/0075173 A1* | 3/2018 | Stomakhin | ................ | G06F 30/20 |
| 2019/0332733 A1* | 10/2019 | Ji | ................ | G06F 30/23 |
| 2020/0104439 A1* | 4/2020 | Ishihara | ................ | G06F 30/25 |
| 2020/0342151 A1* | 10/2020 | Misawa | ................ | G06F 30/25 |
| 2020/0401747 A1* | 12/2020 | Ishihara | ................ | G16Z 99/00 |

FOREIGN PATENT DOCUMENTS

| | | | |
|---|---|---|---|
| CN | 104636538 | 5/2015 | |
| JP | 2000-322407 | 11/2000 | |
| JP | 2013-210918 | 10/2013 | |
| JP | 2020-057135 | 4/2020 | |
| JP | 2020-064450 | 4/2020 | |
| JP | 2020-181393 | 11/2020 | |
| WO | WO-2021246378 A1 * | 12/2021 | ......... G01N 15/1012 |

OTHER PUBLICATIONS

Sakai et al. ("Verification and validation of a coarse grain model of the DEM in a bubbling fluidized bed", Chemical Engineering Journal 244 (2014) 33-43) (Year: 2014).*

Queteschiner et al. ("Adaptive Coarse-Graining for Large-Scale DEM Simulations", 12th International Conference on CFD in Oil & Gas, Metallurgical and Process Industries, 2017, pp. 1-6) (Year: 2017).*

International Search Report dated Aug. 10, 2021 with respect to PCT/JP2021/020745.

M. Yamanoi et al., "DEM Simulation Based on Scaling Rule", J. Soc. Powder Technol, Japan, vol. 55 No. 2 (2018), pp. 95-103, doi: 10.4164/sptj.55.95, with English Abstract.

A. V. Patil et al., "Comparison of CFD-DEM heat transfer simulations with infrared/visual measurements", Chemical Engineering Journal 277 (2015), The Netherlands, pp. 388-401.

H. Setouchi, "The Discrete Element Model Introduced the Rotational Stiffness Between the Spherical Elements", Japan Society of Civil Engineers collected papers A2 (applied mechanics), vol. 68, No. 1, pp. 18-29, 2012, Japan, with English Abstract.

M. Sakai, "How Should the Discrete Element Method Be Applied in Industrial Systems?: A Review", KONA Powder Part. J. No. 33, pp. 169-178(2016).

L. Lu et al., "Extension of a coarse grained particle method to simulate heat transfer in fluidized beds", Int. J. Heat Mass Transf. vol. 111, pp. 723-735(2017).

* cited by examiner

SIMULATION DEVICE, SIMULATION METHOD, AND PROGRAM

CROSS-REFERENCE TO RELATED APPLICATIONS

This application is a continuation-in-part application of International Application No. PCT/JP2021/020745 filed on May 31, 2021, and designating the U.S., which is based upon and claims priority under Japanese Patent Application No. 2020-95620 filed Jun. 1, 2020, and Japanese Patent Application No. 2020-162719 filed Sep. 28, 2020, the entire contents of which are incorporated herein by reference.

BACKGROUND

1. Technical Field

The present invention relates to a simulation device, a simulation method, and a program.

2. Description of the Related Art

Patent Literature 1 discloses a simulation apparatus including an input apparatus that performs an input of a simulation condition, an output apparatus that performs an output of a simulation result, and a processing apparatus that analyzes behavior of a granular material that includes a plurality of particles having different sizes based on the simulation condition input from the input apparatus, wherein the processing apparatus obtains the behavior of a coarse-view granular material by a simulation based on a value of a parameter that defines a particle diameter distribution of a granular material to be simulated and a value of a coarse-view coefficient which is a reference for coarsely viewing the particles, which are input from the input apparatus, and associates the behavior of the particles obtained by the simulation with the input value of the coarse-view coefficient and outputs the result to the output apparatus.

RELATED-ART DOCUMENTS

Patent Documents

Japanese Laid-Open Patent Publication No. 2020-57135

SUMMARY

To improve processes in factories and reduce the number of test steps when reviewing a manufacturing process, attempts have been made to analyze the behavior of granular material including multiple particles (granular material particles) using a discrete element method (DEM) calculation, or the like.

The discrete element method calculation is a simulation technique that describes the movement of the granular material as a whole by solving an equation of motion for each particle.

However, in discrete element method calculations, as the number of particles to be handled increases, the calculation load increases. For this reason, when analyzing a behavior of a granular material on a large scale, such as that of a plant used in a factory, since the amount of calculation becomes vast in size, in practice, it becomes difficult to perform the calculations.

Therefore, a simulation apparatus using a coarse-view method using a particle group including multiple particles as a single coarse-view particle has been studied (see Patent Document 1). The simulation apparatus using the coarse-view method requires the appropriate selection of parameters for the coarse-view particle to be used in the calculation in order to obtain accurate analysis results. Therefore, there was a need for a new simulation device capable of selecting and setting parameters for coarse-view particles using a new method and analyzing the behavior of the granular material including multiple particles.

In view of the above-described problems in the related art, an object of the present invention is to provide a new simulation device capable of analyzing a behavior of a granular material including multiple particles.

In order to solve the above problem, an aspect of the present invention is to provide a simulation device for analyzing a behavior of a granular material including a plurality of particles. The simulation device includes a first parameter acquisition unit that acquires a first parameter including a parameter related to the granular material, a second parameter calculation unit that calculates a second parameter, when a particle group including the plurality of particles is coarsely viewed to form a single coarse-view particle, the second parameter being a parameter with respect to the coarse-view particle, and a coarse-view particle behavior analysis unit that analyzes a behavior of the coarse-view particle based on the first parameter and the second parameter. The second parameter calculation unit calculates the second parameter by solving a characteristic equation that uses a relationship between an elastic energy of the particle group and an elastic energy of the coarse-view particle.

DETAILED DESCRIPTION

Specific examples of a simulation device, a simulation method, and a program according to an embodiment of the present disclosure (hereinafter referred to as the "present embodiment") are described below with reference to the drawings. It should be noted that the present invention is not limited to these examples, but is indicated by the claims and is intended to include all modifications within the meaning and scope equal to the claims.

1. First Embodiment

<Simulation Device>
(1) Parameter Used for Coarse-View Particle and Calculating Particle Behavior of Coarse-View Particle
(1-1) Coarse-View of Particle Before describing the details of the simulation device of the present embodiment, a method of coarsely viewing a particle group including multiple particles and calculating a parameter related to the coarse-view particle, which can be used in the simulation device of the present embodiment, will be described below.

As described above, in the discrete element method calculation, as the number of particles to be handled increases, the calculation load increases. For this reason, when analyzing a behavior of a granular material on a large scale, such as that of a plant used in a factory, since the amount of calculation becomes vast in size, in practice, it becomes difficult to perform the calculations.

Figure 1A:
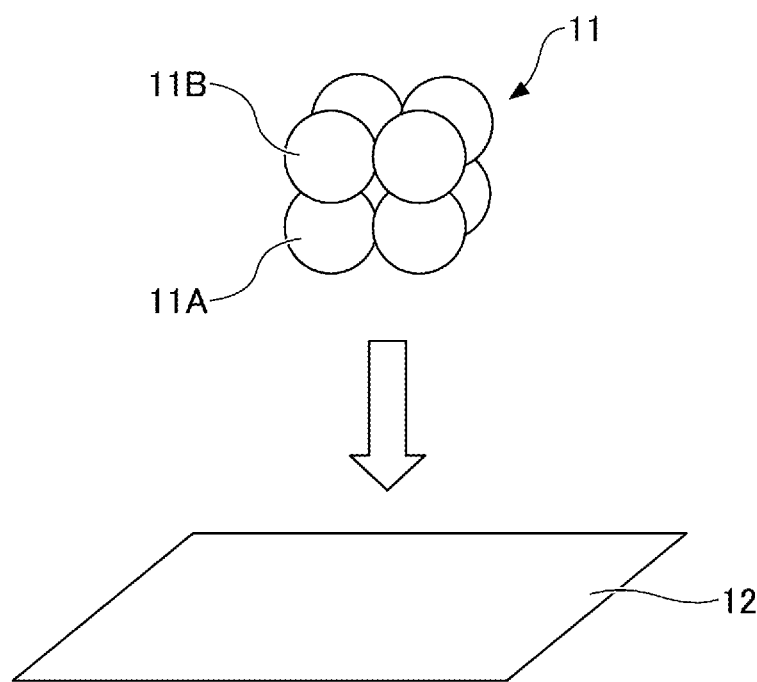
FIG. 1A is an explanatory diagram illustrating a collision between a particle group including multiple particles and a wall.
Figure 2A:
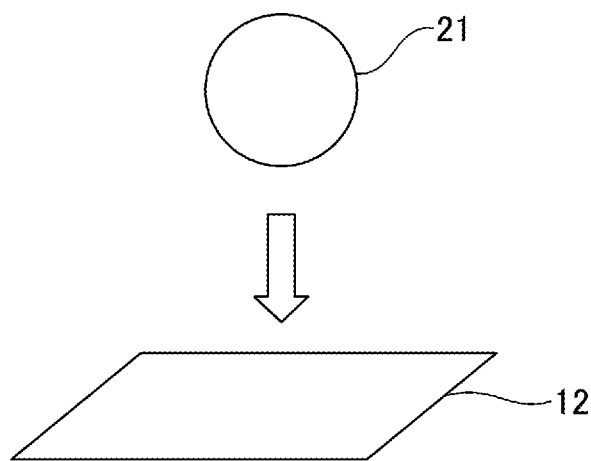
FIG. 2A is an explanatory diagram illustrating a coarse-view particle in which a particle group including multiple particles is coarsely viewed, and a collision of the coarse-view particle with a wall.

Therefore, when analyzing a behavior of a granular material including a large number of particles, in order to reduce the amount of calculation, for example, a technique of coarse-view, in which a particle group 11 including multiple particles illustrated in FIG. 1A is treated as a coarse-view particle 21 which is a single large particle, as illustrated in FIG. 2A, is required.

However, some parameters required for the calculation will change because the specific surface area or the like is different between the individual particles before being coarsely viewed and the coarse-view particle. Therefore, a parameter of the coarse-view particle is required to be determined appropriately.

(1-2) Parameter Used to Calculate Particle Behavior of Coarse-View Particle

Therefore, the inventors of the present invention investigated a method of determining a parameter related to the coarse-view particle. In the calculation, a model was used in which a particle group 11 including multiple particles before being coarsely viewed, which is illustrated in FIG. 1A collided with a wall surface 12 and in which the coarse-view particle 21 illustrated in FIG. 2A collided with the wall surface 12. The following description describes a method of determining the parameter of the coarse-view particle by using the case where there is collision between the wall surface and one particle. However, description regarding a case where when particles collide with each other will be omitted because the description is substantially the same.

As illustrated in FIG. 1A, suppose that a particle group 11 including multiple particles is arranged in a cubic shape with two particles each in a vertical direction, a horizontal direction, and a height direction, for a total of $2^3$ particles. As will be described later, when the eight particles are combined into a single coarse-view particle, the number of particles arranged in one side direction, i.e., 2, is used as a coarse-view magnification.

Figure 1B:
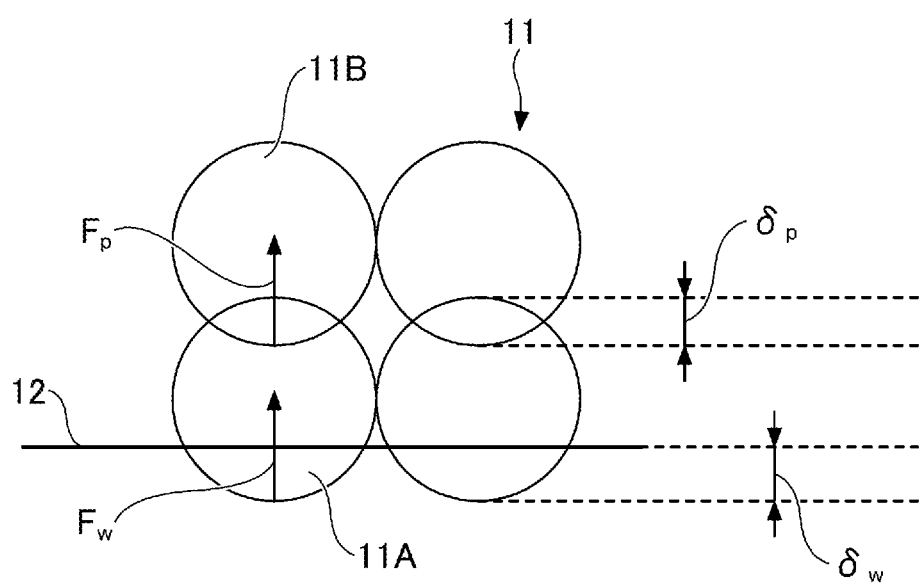
FIG. 1B is an explanatory diagram illustrating the collision between the particle group including multiple particles and the wall.

When the particle group 11 including multiple particles 11A and 11B illustrated in FIG. 1A collides with the wall surface 12, the force that the particle 11A located on the wall surface 12 side of the particle group 11 receives from the wall surface or from an external particle is designated as $F_w$ as illustrated in FIG. 1B. Further, as illustrated in FIG. 1B, the amount of overlap of the particle 11A with the wall surface 12 or with the external particle is denoted as $\delta_w$, and the amount of overlap of the particle 11B with adjacent particle 11A is denoted as op. FIG. 1B is a side view when the particle group 11 collides with the wall surface 12.

In this case, the magnitude of the force applied to the particle group 11 can be expressed by the following Formula (1)

Note that α in Formula (1) denotes the coarse-view magnification, which means the number of particles arranged in one side direction when the particle group 11 is made into a single coarse-view particle as described above. If the particle group 11 illustrated in FIG. 1A is made into the single coarse-view particle 21 illustrated in FIG. 2A, then α=2.

Also, m denotes the mass of each particle 11A and 11B, $a_G$ denotes the acceleration of a center of gravity of the particle group 11, and $\eta_w$ denotes the viscosity coefficient calculated from the restitution between the wall surface 12 or the external particle and the particle 11A. The contact force between the particles is eliminated due to the law of action-reaction, so that the force $F_p$ received by the particle 11B, which is not in direct contact with the wall surface 12, from the adjacent particle 11A will not appear in Formula (1).

[Math 1]

$$\alpha^3 ma_G = \alpha^2 F_w - \alpha^2 \eta_w \dot{\delta}_w \quad (1)$$

Further, the relationship between a restitution e and a viscosity coefficient η, which is used when calculating the above-mentioned $\eta_w$ or the like from the restitution, can be expressed by the following Formula (A). In Formula (A), m* denotes a converted mass and K denotes a spring coefficient.

[Math 2]

$$\eta = -2\log e \frac{\sqrt{m_* K}}{\sqrt{\pi^2 + (\log e)^2}} \quad (A)$$

Next, as illustrated in FIG. 2A, the particle group 11 including eight particles illustrated in FIG. 1A is assumed to be a single coarse-view particle 21. In this case, when the coarse-view particle 21 collides with the wall surface 12, the force that the coarse-view particle 21 receives can be expressed by the following Formula (2).

Figure 2B:
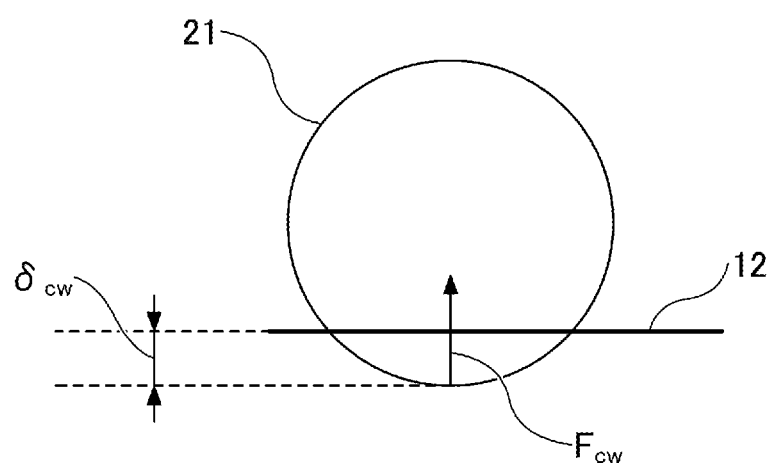
FIG. 2B is an explanatory diagram illustrating the coarse-view particle in which the particle group including multiple particles is coarsely viewed, and the collision of the coarse-view particle with the wall.

In Formula (2), $F_{cw}$ denotes the force that the coarse-view particle 21 receives from the wall surface 12 or the external particle, $\delta_{cw}$ denotes the amount of overlap of the coarse-view particle 21 with the wall surface 12 or with the external particle, and $\delta_{cw}$ denotes the viscosity coefficient calculated from the restitution between the coarse-view particle 21 and the wall surface 12 or the external particle, as illustrated in FIG. 2B. FIG. 2B is a side view when the coarse-view particle 21 collides with the wall surface 12.

[Math 3]

$$\alpha^3 ma_G = F_{Cw} - \eta_{Cw} \dot{\delta}_{Cw} \quad (2)$$

As described above, coarse-view is performed to reduce the amount of calculation in the discrete element method calculation. Therefore, the calculated result for the coarse-view particle 21 is consistent with the calculated result for the particle group 11 before the coarse-view particle 21 is coarsely viewed.

Therefore, the following Formula (3) and Formula (4) are derived from Formula (1) calculated for the particle group 11 and Formula (2) calculated for the coarse-view particle 21. Formula (3) and Formula (4) indicate that the corresponding parameters match.

[Math 4]

$$F_{Cw} = \alpha^2 F_w \quad (3)$$

[Math 5]

$$\eta_{Cw} \dot{\delta}_{Cw} = \alpha^2 \eta_w \dot{\delta}_w \quad (4)$$

Further, by using the Hertz-Mindlin contact model, the force applied to each particle can be expressed as the following Formula (5) to Formula (7) using the amount of overlap $\delta_w$, $\delta_p$, and $\delta_{cw}$ of the particle. In Formula (5) to Formula (7), $K_w$ denotes the spring coefficient between the particle 11A and the wall surface 12 or the external particle, $K_p$ denotes the spring coefficient between the internal particle of the particle group 11, and $K_{cw}$ denotes the spring coefficient between the coarse-view particle 21 and the wall surface 12 or the external particle.

[Math 6]

$$F_w = -K_w \delta_w^{\frac{3}{2}} \quad (5)$$

[Math 7]

$$F_p = -K_p \delta_p^{\frac{3}{2}} \quad (6)$$

[Math 8]

$$F_{cw} = -K_{cw} \delta_{cw}^{\frac{3}{2}} \quad (7)$$

Then, the following relation of Formula (8) is derived from Formula (3), Formula (5), and Formula (7).

[Math 9]

$$-K_{cw} \delta_{cw}^{\frac{3}{2}} = -\alpha^2 K_w \delta_w^{\frac{3}{2}} \quad (8)$$

By defining $K_r$ as in Formula (9) below, Formula (8) can be expressed as in Formula (10) below.

[Math 10]

$$K_r \stackrel{def}{=} \frac{K_{cw}}{\alpha^2 K_w} \quad (9)$$

[Math 11]

$$\delta_w = K_r^{\frac{2}{3}} \delta_{cw} \quad (10)$$

If the center of gravity of the particle group 11 before being coarsely viewed and the coarse-view particle 21 coincide, the following relation of Formula (11) is satisfied.

[Math 12]

$$\delta_w + \frac{1}{2}(\alpha - 1)\delta_p = \delta_{cw} \quad (11)$$

Therefore, by appropriately setting $K_r$, it can also be seen that the amount of overlap of the particles constituting the particle group 11 before being coarsely viewed can be calculated from the amount of overlap $\delta_{CW}$ of the coarse-view particle 21 and the wall surface 12 or the external particle.

Then, $K_r$ can be calculated by the characteristic equation using the relationship between the elastic energy of the particle group 11 before being coarsely viewed during the collision and the elastic energy of the coarse-view particle 21. Specifically, for example, a characteristic equation can be created to calculate $K_r$ on the assumption that the elastic energy of the entire particle group 11 before being coarsely viewed is equal to the elastic energy of the entire coarse-view particle.

The elastic energy of the particle group 11 and the coarse-view particle colliding with the wall surface 12 can be calculated by integrating Formula (5) to Formula (7), which express the force applied to the particles 11A and 11B constituting the particle group 11 and the force applied to the coarse-view particle, at the distance of the amount of overlap.

Therefore, using the elastic energy of the entire particle group 11 before being coarsely viewed and the elastic energy of the entire coarse-view particle, the following Formula (12) is obtained.

[Math 13]

$$\frac{2}{5}\alpha^2 K_w \delta_w^{\frac{5}{2}} + \frac{2}{5}(\alpha-1)\alpha^2 K_p \delta_p^{\frac{5}{2}} = \frac{2}{5}K_{cw}\delta_{cw}^{\frac{5}{2}} \qquad (12)$$

The above Formula (12) can be transformed into the following Formula (13) using the aforementioned Formula (8) to Formula (11).

[Math 14]

$$K_r^{\frac{5}{3}} + (\alpha-1)\frac{K_p}{K_w}\left(2\left(1-K_r^{\frac{2}{3}}\right)/\alpha-1\right)^{\frac{5}{2}} - K_r = 0 \qquad (13)$$

Formula (13) is a characteristic equation of $K_r$ in the vertical direction. Further, as it is clear from the defining equation of Formula (9), $K_r$ is a parameter related to the amount of overlap between the coarse-view particle and the particle constituting the particle group 11 before being coarsely viewed and is a parameter controlling the behavior of the coarse-view particle. Therefore, by obtaining $K_r$ in advance by the characteristic equation, it becomes possible to calculate a parameter with respect to the coarse-view particle, such as calculating the amount of overlap of a particle group before being coarsely viewed from the amount of overlap of the coarse-view particle, and to calculate the behavior of the coarse-view particle.

Heretofore, although the equation of motion in the vertical direction with respect to the wall surface 12 has been used for explanation, the same applies to an equation of motion in the tangential direction and to an equation of motion in the rotation.

Specifically, an equation of motion in the tangential direction can be expressed by Formula (14).

In this case, when $K_r$ is set as illustrated in Formula (15), $\delta_w$ and $\delta_p$ can be expressed as Formula (16) and Formula (17). If the elastic energy of the particle group before being coarsely viewed is equal to the elastic energy of the coarse-view particle, Formula (18) is obtained. Formula (19), which is a characteristic equation in the tangential direction can be obtained by modifying Formula (18). However, a linear spring model was used for the contact model in the tangential direction. As described above, although the formula for calculating the elastic energy varies depending on the contact model, the elastic energy can be appropriately calculated by changing the characteristic equation as necessary.

[Math 15]

$$\alpha^3 ma_{cw} = -\alpha^2 K_w \delta_w - \alpha^2 \eta_w \dot\delta_w \qquad (14)$$

[Math 16]

$$K_r \stackrel{def}{=} \frac{K_{cw}}{\alpha^2 K_w} \qquad (15)$$

[Math 17]

$$\delta_w = K_r \delta_{cw} \qquad (16)$$

[Math 18]

$$\delta_p = 2(1-K_r)\delta_{cw}/\alpha - 1 \qquad (17)$$

[Math 19]

$$\frac{1}{2}\alpha^2 K_w \delta_w^2 + (\alpha-1)\alpha^2 \frac{1}{2}K_p \delta_p^2 = \frac{1}{2}K_{cw}\delta_{cw}^2 \qquad (18)$$

[Math 20]

$$K_r^2 + (\alpha-1)\frac{K_p}{K_w}\left(2(1-K_r)/\alpha - 1\right)^2 = K_r \qquad (19)$$

The equation of motion of rotation will be described in detail in a second embodiment.

(1-3) Parameter Related to Heat Transfer of Coarse-View Particle

The aforementioned $K_r$ can also be used to determine the thermal conductivity, which is a parameter related to the heat transfer of the coarse-view particle.

The heat transfer of the particle is described by the following Formula (20) and Formula (21) by using the thermal conductivity.

In Formula (20) and Formula (21), Q denotes the heat flow rate, h denotes the heat flow coefficient, $\Delta T$ denotes the temperature difference between the wall surfaces or between the particles, $K_w$ denotes the thermal conductivity between the wall surface 12 or the external particles and the particle 11A, $K_p$ denotes the thermal conductivity inside the particle group 11, and a denotes the contact radius of the particle group 11.

[Math 21]

$$Q = h\Delta T \qquad (20)$$

[Math 22]

$$h = \frac{k_w k_p}{k_w + k_p} a \qquad (21)$$

Since the contact radius between the particle and the wall surface or another particle changes according to the particle size, as the particle size increases, the heat flow rate applied to the particle changes, which affects the temperature change of the particle.

The contact radius depends on the amount of overlap of each particle. Further, as described above, the amount of overlap before and after the coarse-view is related to the solution of the characteristic equation in the vertical direction. Therefore, when the heat transfer equation is rewritten by using the solution $K_r$ of the characteristic equation in the vertical direction, the following Formula (22) and Formula (23) are obtained.

In Formula (23), a' denotes the contact radius of the coarse-view particle and r denotes the radius of the particle constituting the particle group 11.

[Math 23]

$$Q = \alpha^2 h\Delta T \qquad (22)$$

[Math 24]

$$h = \frac{k_w k_p}{k_w + k_p}a' = \frac{k_w k_p}{k_w + k_p}\sqrt{2r\delta_w} = \frac{k_w k_p}{k_w + k_p}\sqrt{2rK_r^{\frac{3}{2}}\delta_{cw}} \qquad (23)$$

Then, the heat transfer equation of the coarse-view particle can be expressed by the following Formula (24) and Formula (25).

In Formula (24) and Formula (25), $Q_c$ denotes the heat flow rate of the coarse-view particle, $h_c$ denotes the heat flow coefficient of the coarse-view particle, $\Delta T_c$ denotes the temperature difference between the coarse-view particle 21 and the wall surface 12 or the external particle, $K'_w$ denotes the thermal conductivity between the wall surface 12 and the coarse-view particle 21, and K'p denotes the thermal conductivity between the external particle and the coarse-view particle.

[Math 25]

$$Q_c = h_c \Delta T_c \quad (24)$$

[Math 24]

$$h = \frac{k'_w k'_p}{k'_w + k'_p} d' = \frac{k'_w k'_p}{k'_w + k'_p} \sqrt{2\alpha r \delta_{cw}} \quad (25)$$

Focusing on thermal conductivity, by using $K_r$ to convert the thermal conductivity before and after the coarse-view into the following Formula (26) and Formula (27), the equivalent heat conduction equation before and after the coarse-view can be obtained. Note that $\Delta T_c = \propto \Delta T$.

[Math 27]

$$k'_w = K_r^{\frac{1}{3}} \alpha^{\frac{1}{2}} k_w \quad (26)$$

[Math 28]

$$k'_p = K_r^{\frac{1}{3}} \alpha^{\frac{1}{2}} k_p \quad (27)$$

In other words, when performing coarse-view, by multiplying the thermal conductivity by $K_r^{1/3} \alpha^{1/2}$, the heat flow rate given to the particle group before being coarsely viewed and the heat flow rate given to the particle after being coarsely viewed can be made the same. As a result, the time change of temperature can be made to match before and after coarse-view.

Note that, although the thermal conductivity before and after the coarse-view is explained here as an example, parameters other than the thermal conductivity can be calculated similarly after being coarsely viewed, by using the solution $K_r$ of the aforementioned characteristic equation. For example, the coefficient of restitution, the coefficient of friction and the coefficient of rolling friction can be calculated using a characteristic equation. Further, depending on the model used in the calculation, these coefficients are adjustable and can be calculated and converted using the characteristic equation as described above.

(2) Simulation Device

The simulation device of the present embodiment is a simulation device for analyzing the behavior of a granular material including multiple particles and can have the following members. A first parameter acquisition unit acquires a first parameter including a parameter related to a granular material. A second parameter calculation unit calculates a second parameter, which is a parameter for a coarse-view particle, when a particle group including multiple particles is coarsely viewed to form a single coarse-view particle. A coarse-view particle behavior analysis unit analyzes the behavior of the coarse-view particle based on the first parameter and the second parameter.

The second parameter calculation unit calculates the second parameter by using a solution of the characteristic equation that uses a relationship between an elastic energy of the particle group and an elastic energy of the coarse-view particle.

Figure 3:
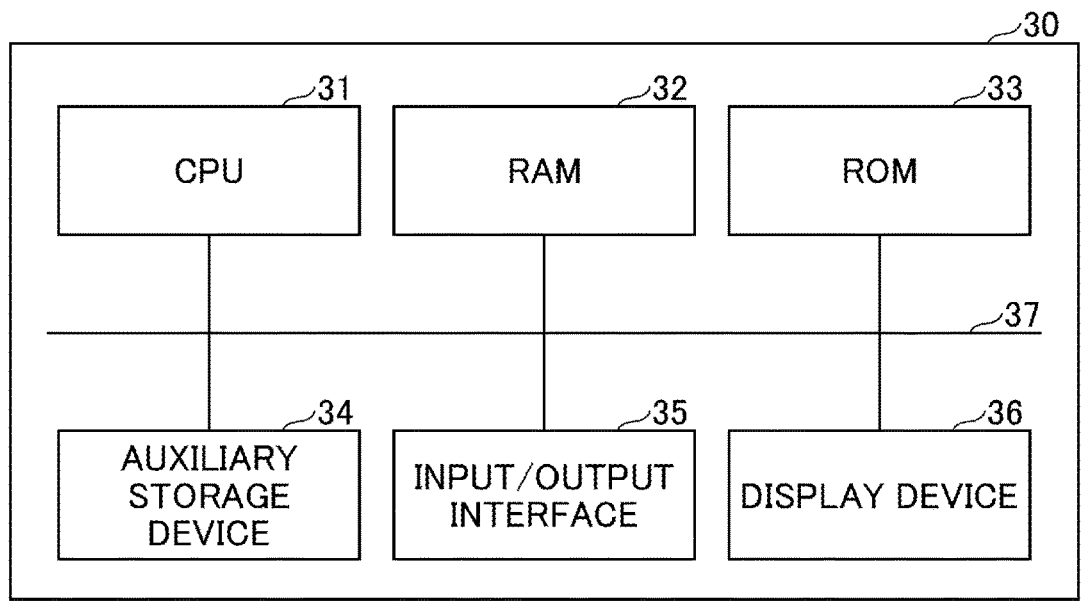
FIG. 3 is a hardware configuration diagram of a simulation device according to an embodiment of the present invention.

As illustrated in the hardware configuration diagram illustrated in FIG. 3, a simulation device 30 of the present embodiment, for example, includes an information processing unit (computer), and can be physically configured as a computer system including a Central Processing Unit (processor) (CPU) 31 as an arithmetic processing unit, a Random Access Memory (RAM) 32 or a Read only Memory (ROM) 33 as a main storage device, an auxiliary storage device 34, an input/output interface 35, and a display device 36 as an output device. These are interconnected by a bus 37. The auxiliary storage device 34 and the display device 36 may be provided externally.

The CPU 31 controls the overall operation of the simulation device 30 and performs various kinds of information processing. The CPU 31 can calculate the second parameter, which is a parameter for the coarse-view particle, and analyze the behavior of the coarse-view particle by executing, for example, a simulation method described later or a program (simulation program) stored in the ROM 33 or the auxiliary storage device 34.

The RAM 32 is used as a work area for the CPU 31 and may include a nonvolatile RAM that stores key control parameters and information.

The ROM 33 can store a program (simulation program) or the like.

The auxiliary storage device 34 is a storage device such as a Solid State Drive (SSD) or a Hard Disk Drive (HDD) and can store various data, files, or the like, necessary for the operation of the simulation device.

The input/output interface 35 includes both a user interface such as a touch panel, keyboard, display screen, and operation buttons, and a communication interface that takes in information from an external data storage server and outputs analysis information to other electronic devices.

The display device 36 is a monitor display or the like. In the display device 36, an analysis screen is displayed, and the screen is updated according to input/output operations via the input/output interface 35.

Each function of the simulation device 30 illustrated in FIG. 3 can be implemented by reading a program (simulation program) or the like from a main storage device such as RAM 32 or ROM 33 or an auxiliary storage device 34 and executing it by the CPU 31, thereby reading and writing data from and to the RAM 32 or the like, and operating the input/output interface 35 and the display device 36.

Figure 4:
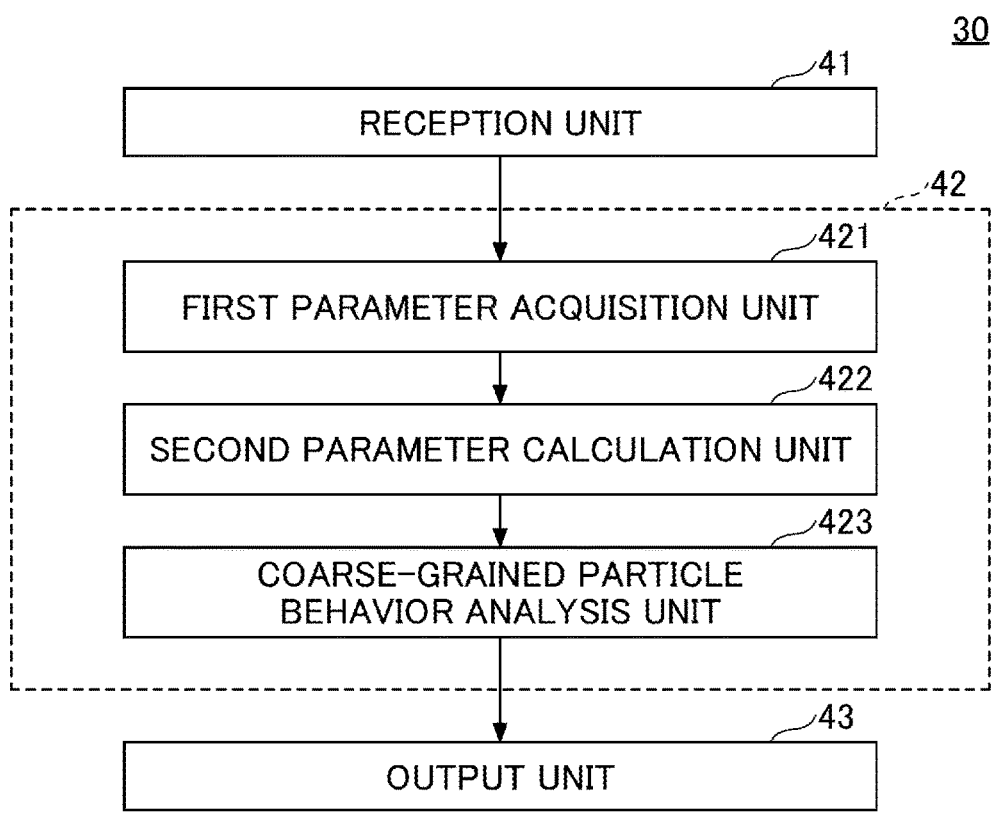
FIG. 4 is a block diagram illustrating functions of the simulation device according to an embodiment of the present invention.

FIG. 4 illustrates a functional block diagram of the simulation device 30 of the present embodiment.

As illustrated in FIG. 4, the simulation device 30 may include a reception unit 41, a processing device 42, and an output unit 43. Each of these parts is an information processing device such as a personal computer provided with a CPU, a storage device, and various interfaces of the simulation device 30, and is realized in cooperation with software and hardware by executing, for example, a simulation method and a program which will be described later in which the CPU is stored in advance.

The configuration of each part will be described below.

(A) Reception Unit

The reception unit 41 receives input of commands and data from a user related to the processing executed by the processing device 42. For example, the reception unit 41 includes a keyboard or a mouse for operated by a user and inputting a command or the like, a communication device for inputting the command or the like through a network, and a reading device for inputting the command or the like from various storage media such as a CD-ROM or a DVD-ROM.

(B) Processing Device

The processing device 42 may include a first parameter acquisition unit 421, a second parameter calculation unit 422, and a coarse-view particle behavior analysis unit 423. It should be noted that the processing device may include further optional members as needed, for example, an initial setting unit or the like.

(B-1) First Parameter Acquisition Unit

In the first parameter acquisition unit 421, for example, a first parameter including a parameter related to a granular material to be analyzed can be acquired. The first parameter may include various parameters required for the analysis in addition to the parameter associated with the granular material. Since the first parameter can be selected depending on the content of the analysis (simulation), the specific type is not particularly limited. The first parameter includes various parameters required for the discrete element method calculation, specifically one or more parameters selected from, for example, particle size, particle number, Young's modulus, time step of calculation, Poisson's ratio, friction coefficient with wall surface, friction coefficient between particles, rolling friction coefficient, density, and the like.

The first parameter may be data stored in a database or the like, or an experimental value obtained by performing an experiment in advance. Further, the first parameter may be a calculated value obtained by fitting the experimental results by simulation or the like.

(B-2) Second Parameter Calculation Unit

As described above, in the simulation device 30 of the present embodiment, in order to reduce the amount of calculation, a particle group including multiple particles in the granular material can be coarsely viewed into a single coarse-view particle and the calculation can be performed with a smaller number of particles. However, the coarse-view particle differs in various parameters such as mass from the individual particles constituting the particle group before being coarsely viewed. Therefore, it is necessary to calculate and set the parameters required for the calculation of the coarse-view particle.

In the second parameter calculation unit 422, as described in "(1) Parameter used for coarse-view particle and calculating particle behavior of coarse-view particle", the second parameter can be calculated using $K_r$, which is the solution of the characteristic equation derived using the relationship between the elastic energy of the particle group before being coarsely viewed and the elastic energy of the coarse-view particle. Specifically, for example, assuming that the elastic energy of the entire particle group 11 before being coarsely viewed is equal to the elastic energy of the entire coarse-view particle, the aforementioned characteristic equation of $K_r$ in the vertical direction (i.e., Formula (13)) can be derived and $K_r$ in the vertical direction can be calculated from Formula (13). Then, the second parameter can be calculated by using $K_r$ in the vertical direction, which is the solution of the characteristic equation, in Formula (13). Further, $K_r$ in the tangential direction can be calculated by using the characteristic equation of $K_r$ in the tangential direction in Formula (19), and the second parameter can be calculated using such $K_r$ in the tangential direction.

As described above, $K_r$ is a parameter that controls the behavior of the coarse-view particle, and by using $K_r$, various parameters related to the behavior of the coarse-view particle can be calculated.

The type of the second parameter used in the coarse-view particle behavior analysis unit described later is not particularly limited because the type of the second parameter can be selected according to the content of the analysis. For example, the second parameter may also include the thermal conductivity of the coarse-view particle. In this case, the second parameter calculation unit can calculate the thermal conductivity using the solution $K_r$ of the aforementioned characteristic equation.

(B-3) Coarse-View Particle Behavior Analysis Unit

In the coarse-view particle behavior analysis unit 423, the behavior of the coarse-view particle can be analyzed using the first parameter acquired by the first parameter acquisition unit 421 and the second parameter calculated by the second parameter calculation unit 422. Specifically, the behavior of the coarse-view particle can be analyzed using the discrete element method. The behavior of the granular material can be analyzed by analyzing the behavior of the coarse-view particle.

It should be noted that the behavior here includes not only the change in position due to the motion of the coarse-view particle, but also the state change such as temperature change.

(B-4) Initial Setting Unit

An initial setting unit (not illustrated) can initialize the position of the particles constituting the granular material to be analyzed, and set conditions for analysis, such as the temperature of the area where the granular material is to be placed, if necessary. For example, in a case where the initial conditions are set in advance in a program or the like used for analyzing the behavior of the coarse-view particle in the coarse-view particle behavior analysis unit 423, or in a case where the data is acquired by the first parameter acquisition unit 421, the initial setting unit may be omitted.

(C) Output Unit

The output unit 43 may include a display or the like. The simulation result obtained by the coarse-view particle behavior analysis unit 423 can be output to the output unit 43. The content of the simulation result to be output is not particularly limited, but for example, the position of the coarse-view particle can be output to the output unit 43 as an image in time series and displayed. Further, for example, a time series change of the temperature distribution of the granular material can be output to the output unit 43 as an image and displayed.

According to the simulation device of the present embodiment described above, it is possible to simulate the behavior of a granular material including multiple particles, and the use thereof is not particularly limited. For example, it can be suitably used to simulate the behavior of the granular material in a rotating body such as a kiln. That is, the simulation device of the present embodiment can also analyze the behavior of the granular material in the rotating body.

According to the simulation device of the present embodiment described above, the amount of calculation can be reduced by making a particle group including multiple particles into a single coarse-view particle. Therefore, it is possible to reduce the amount of calculation and efficiently calculate the behavior of the granular material on a large scale, such as that of a plant used in a factory.

Since the parameter of the coarse-view particle is calculated by using the aforementioned parameter $K_r$, the calculation can be performed with high accuracy.

The simulation device of the present embodiment may further include a granular material supply device, a reaction furnace, a controller, or the like, to perform various manufacturing processes using the granular material by using the simulation results.

The granular material supply device includes a device such as a hopper that can store and discharge granular material. The granular material supply device may further have a feeder, a valve, or other supply controller to control the amount of granular material discharged and supplied from the hopper or the like to the reaction furnace. Based on the simulation results, it is preferable to include multiple granular material supply devices each containing granular materials of different physical properties, such as granular materials of a desired average particle size.

Examples of the reaction furnace include various reaction furnaces such as heating furnaces, and rotary furnaces such as kilns. The granular material supply device and the reaction furnace can be connected by piping.

The controller can control to provide the granular material to the reaction furnace with the desired physical properties, for example, the desired average particle size, based on the obtained results of the behavior of the granular material in the reaction furnace. The controller can also control the heating conditions of the reaction furnace based on the obtained results of the behavior of the granular material in the reaction furnace. Examples of heating conditions include temperature conditions in the reaction furnace, atmospheric conditions, and heating time. Further, various sensors may be provided in the granular material supply device or the reaction furnace to detect the amount of granular material to be supplied, the temperature, and the like, and the measurement results measured at any time may be supplied to the controller. In this case, the controller may control each device based on the obtained measurement data.

The controller may include a CPU, a main storage device, an auxiliary storage device, an input/output interface, and the like, so that the controller can perform data processing such as control conditions and communicate with the granular material supply device and the reaction furnace. The main storage device may include a RAM and a ROM, and the auxiliary storage device may include an SSD and an HDD. The input/output interface may include a communication interface for exchanging control signals and data with the granular material supply device or the reaction furnace. A type of the communication interface is not particularly limited. Both wired and wireless communication methods can be used, for example, a wired local area network (LAN) or a wireless LAN.

As described above, based on the result of the behavior of the granular material in the reaction furnace obtained by the simulation, the granular material of the desired physical properties can be supplied from the granular material supply device and further heated in the reaction furnace under the prescribed heating conditions to increase the reaction rate of the granular material. Further, since the heating conditions can be optimized, the amount of energy used during the reaction can be optimized to improve productivity.

If the simulation device of the present embodiment includes the above granular material supply device or the like, the simulation device can also be called a reactor or the like. Further, the granular material supply device, the reaction furnace, and the controller can be detachable from the unit for analyzing a behavior of a granular material including multiple particles, and the simulation results can be reflected in the controller and then used separately.

<Simulation Method>

Next, a simulation method of the present embodiment will be described. The simulation method of the present embodiment can be performed using, for example, the aforementioned simulation device. Therefore, the explanation shall be omitted for some of the matters already explained.

Figure 5:
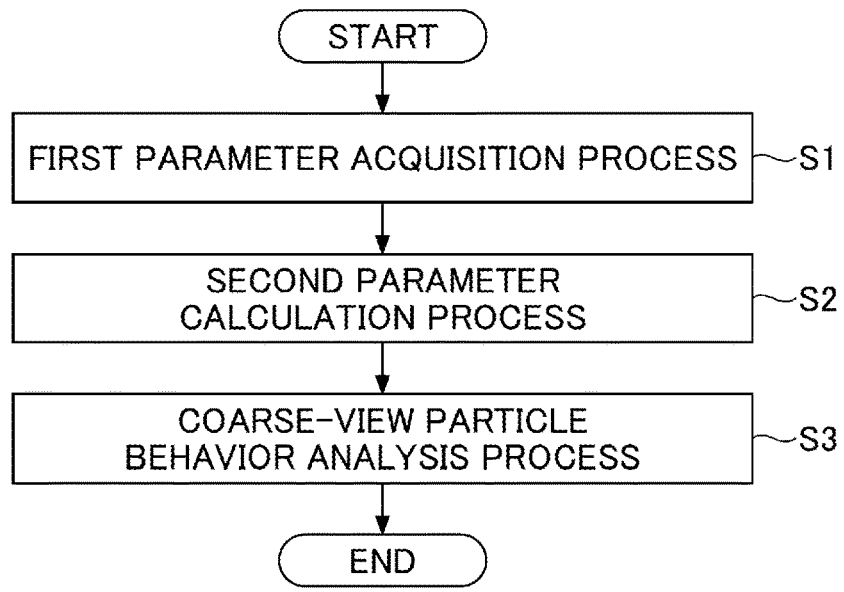
FIG. 5 is a flowchart illustrating a simulation method according to an embodiment of the present invention.

The simulation method of the present embodiment relates to a simulation method of analyzing a behavior of a granular material including multiple particles. The simulation method of the present embodiment can be performed according to the flow diagram illustrated in FIG. 5 and may include the following processes.

The simulation method of the present embodiment may include a first parameter acquisition process (S1) for acquiring a first parameter including a parameter related to a granular material; a second parameter calculation process (S2) for calculating a second parameter, which is a parameter for a coarse-view particle, when a particle group including multiple particles is coarsely viewed to form a single coarse-view particle; a coarse-view particle behavior analysis process (S3) for analyzing a behavior of the coarse-view particle based on the first parameter and the second parameter. In the second parameter calculation process (S2), the second parameter can be calculated by using a solution of a characteristic equation using a relationship between an elastic energy of the particle group and an elastic energy of the coarse-view particle.

Each process is described below.

(1) First Parameter Acquisition Process (S1)

In the first parameter acquisition process (S1), a first parameter including a parameter related to a granular material to be analyzed can be acquired. When the aforementioned simulation device is used, for example, the first parameter acquisition process can be performed in the first parameter acquisition unit 421.

Since the first parameter can be selected depending on the content of the analysis, the specific type is not particularly limited. The first parameter may be various parameters required for the discrete element method calculation. Because a specific example of the first parameter has already been described with respect to the simulation device, the description will be omitted here.

The first parameter may be data stored in a database or the like, or may be an experimental value obtained by performing an experiment in advance. Further, the first parameter may be a calculated value obtained by fitting the experimental results by simulation or the like.

(2) Second Parameter Calculation Process (S2)

In the simulation method of the present embodiment, in order to reduce the amount of calculation, a particle group including multiple particles in the granular material can be coarsely viewed into a single coarse-view particle, and the number of particles can be reduced to perform the calculation.

Therefore, in the second parameter calculation process (S2), as described in "(1) Parameter used for coarse-view particle and calculating particle behavior of coarse-view particle", the second parameter can be calculated using $K_r$, which is the solution of the characteristic equation derived using the relationship between the elastic energy of the particle group before being coarsely viewed and the elastic energy of the coarse-view particle. Specifically, for example, assuming that the elastic energy of the entire particle group 11 before being coarsely viewed is equal to the elastic energy of the entire coarse-view particle, the aforementioned characteristic equation of $K_r$ in the vertical direction (i.e., Formula (13)) can be derived and $K_r$ in the vertical direction can be calculated from Formula (13). Then, the second parameter can be calculated by using $K_r$ in the vertical direction, which is the solution of the characteristic equation in Formula (13). Further, $K_r$ in the tangential direction can be calculated by using the characteristic equation of $K_r$ in the tangential direction in Formula (19), and the second parameter can be calculated using such $K_r$ in the tangential direction.

As described above, $K_r$ is a parameter that controls the behavior of the coarse-view particle, and by using $K_r$, various parameters related to the behavior of the coarse-view particle can be calculated.

When the aforementioned simulation device is used, the second parameter calculation process can be performed in the second parameter calculation unit 422, for example.

The type of the second parameter used in the coarse-view particle behavior analysis process described later is not particularly limited because the type of the second parameter can be selected according to the content of the analysis. For example, the second parameter can also include the thermal conductivity of the coarse-view particle. In this case, the second parameter calculation process can calculate the thermal conductivity using the solution $K_r$ of the aforementioned characteristic equation.

(3) Coarse-View Particle Behavior Analysis Process (S3)

In the coarse-view particle behavior analysis process (S3), the behavior of the coarse-view particle can be analyzed using the first parameter acquired in the first parameter acquisition process (S1) and the second parameter calculated in the second parameter calculation process (S2). Specifically, the behavior of the coarse-view particle can be analyzed using the discrete element method. The behavior of the granular material can be analyzed by analyzing the behavior of the coarse-view particle.

It should be noted that the behavior here includes not only the change in position due to the motion of the coarse-view particle, but also the state change such as temperature change.

(4) Initial Setting Process

The simulation method of the present embodiment may also include, for example, an initial setting process. The initial setting process can initialize the position of the particles constituting the granular material to be analyzed, and set conditions for analysis, such as the temperature of the area where the granular material is to be placed, if necessary. For example, in a case where the initial conditions are set in advance in a program or the like used for analyzing the behavior of the coarse-view particle in the coarse-view particle behavior analysis process, or in a case where the data is acquired by the first parameter acquisition process, the initial setting process may be omitted.

(5) Output Process

The simulation method of the present embodiment may also include an output process, for example. In the output process, for example, the simulation result obtained by the coarse-view particle behavior analysis process (S3) can be output to the output unit. The content of the simulation result to be output is not particularly limited, but for example, the position of the coarse-view particle can be output as an image in time series and displayed. Further, for example, a time series change of the temperature distribution of the granular material can be output to the output unit as an image and displayed.

According to the simulation method of the present embodiment described above, the amount of calculation can be reduced by making a particle group including multiple particles into a single coarse-view particle. Therefore, it is possible to reduce the amount of calculation and efficiently calculate the behavior of the granular material on a large scale, such as that of a plant used in a factory.

Since the parameter of the coarse-view particle is calculated by using the aforementioned parameter $K_r$, the calculation can be performed with high accuracy.

The simulation method of the present embodiment may further include a granular material supply process, a reaction process, or the like, to perform various manufacturing processes using the granular material by using the simulation results.

In the granular material supply process, a granular material can be supplied from the granular material supply device to the reaction furnace based on a result of a behavior of the granular material in the reaction furnace obtained by simulation. In this case, the granular material of a specified physical property selected based on the simulation result can be supplied as the granular material.

Further, in the reaction process, the granular material supplied to the reaction furnace in the granular material supply process can be heated. In this case, the granular material can be heated under prescribed heating conditions based on the simulation result.

As described above, based on the result of the behavior of the granular material in the reaction furnace obtained by the simulation, the granular material of the desired physical properties can be supplied from the granular material supply device and further heated in the reaction furnace under the prescribed heating conditions to increase the reaction rate of the granular material. Further, since the heating conditions can be optimized, the amount of energy used during the reaction can be optimized to improve productivity.

When the simulation method of the present embodiment performs the above granular material supply process or the like, the simulation method may also be a granular material processing method or the like.

<Program>

Next, the program of the present embodiment will be described.

The program of the present embodiment relates to a program for analyzing a behavior of a granular material including multiple particles, and the computer can function as the following parts.

A first parameter acquisition unit acquires a first parameter including a parameter related to the granular material.

A second parameter calculation unit calculates a second parameter, which is a parameter for a coarse-view particle, when a particle group including multiple particles is coarsely viewed to form a single coarse-view particle.

A coarse-view particle behavior analysis unit analyzes a behavior of the coarse-view particle based on the first parameter and the second parameter.

The second parameter calculation unit calculates the second parameter by using a solution of the characteristic equation that uses a relationship between an elastic energy of the particle group and an elastic energy of the coarse-view particle.

The second parameter may also include the thermal conductivity of the coarse-view particles. In this case, the second parameter calculation unit can calculate the thermal conductivity using the solution of the aforementioned characteristic equation.

The program according to the present embodiment can be stored in various storage media of the main storage device or the auxiliary storage device such as the RAM or ROM of the simulation device described above. The program can be read and executed by the CPU to read and write data in the RAM or the like, and the input/output interface and the display device can be operated. For this reason, the description of the matters already described in the simulation device is omitted.

The program of the present embodiment described above may be provided by storing it on a computer connected to a network such as the Internet and downloading it via the network. The program of the present embodiment may be provided and distributed via a network such as the Internet.

The program of the present embodiment may be distributed or distributed while stored in an optical disk such as a CD-ROM or a recording medium such as a semiconductor memory.

According to the program of the present embodiment described above, the amount of calculation can be reduced by making a particle group including multiple particles into a single coarse-view particle. Therefore, it is possible to reduce the amount of calculation and efficiently calculate the behavior of the granular material on a large scale, such as that of a plant used in a factory.

Further, since the parameter of the coarse-view particle is calculated by using the aforementioned parameter $K_r$, the calculation can be performed with high accuracy.

2. Second Embodiment

<Simulation Device>
(1) Parameter Used for Coarse-View Particle and Calculating Particle Behavior of Coarse-View Particle In a second embodiment, when calculating the amount of overlap for the equation of motion in the tangential direction, the point of assuming that the angular momentum and rotational energy coincide before and after coarse-view differs from that of the first embodiment described above. Further, with respect to the equation of motion in the rotational direction, the torque can be calculated using the amount of overlap obtained as described above. This enables the behavior of the particles after coarse-view to be analyzed more accurately while reducing the amount of calculation.

(1-1) Amount of Overlap

Generally, the amount of overlap in the tangential direction is obtained by using the time integral of the tangential component $v_t$ (indicated by an arrow above $v_t$ in the formula below) of the velocity from the start of the contact to the end of the contact. Where t is the time, the vector r (indicated by an arrow above r in the formula below) is the vector from the center of the particles constituting the particle group 11 to the contact point, and the vector w (indicated by an arrow above w in the formula below) is the rotation vector of the particle group 11.

Note that hat t in the following formula (indicated by a hat above t in the formula below) indicates the unit vector of overlap in the tangential direction.

[Math 29]

$$\delta_t \hat{t} = \int_{start}^{end} (\vec{v_t} + \vec{\omega} \times \vec{r}) dt \quad (28)$$

Therefore, each amount of overlap between the particle and the wall surface is expressed by the following Formula (29). Note that the subscript t in the following formula means the tangential component.

[Math 30]

$$\delta_{w,t} \hat{t} = \int_{start}^{end} (\vec{v_{w,t}} + \vec{\omega} \times \vec{r}) dt \quad (29)$$

The amount of overlap between particles can be expressed by the following Formula (30).

[Math 31]

$$\delta_{p,t} \hat{t} = \int_{start}^{end} (\vec{v_{p,t}} + 2\vec{\omega} \times \vec{r}) dt \quad (30)$$

Meanwhile, the amount of overlap of the coarse-view particle 21 is expressed by the following Formula (31). Note that the vector $\omega_{cw}$ (indicated by the arrow above $\delta_{cw}$ in the following formula) is the rotation vector of the coarse-view particle 21.

[Math 32]

$$\delta_{cw,t} \hat{t} = \int_{start}^{end} (\vec{v_{cw,t}} + \vec{\omega_{cw}} \times \alpha \vec{r}) dt \quad (31)$$

Here, as in the case of Formula (11), which is the equation of motion in the vertical direction, if the position of the center of gravity of the particle group 11 before being coarsely viewed and the coarse-view particle 21 coincide, the relationship of Formula (32) below is satisfied.

[Math 33]

$$\begin{aligned}
\delta_{w,t}\hat{t} + \frac{1}{2}(\alpha - 1)\delta_{p,t}\hat{t} &\\
&= \int_{start}^{end} \left\{ \vec{v_{w,t}} + \frac{1}{2}(\alpha - 1)\vec{v_{p,t}} + \alpha\vec{\omega} \times \vec{r} \right\} dt \\
&= \int_{start}^{end} (\vec{v_{cw,t}} + \alpha\vec{\omega_{cw}} \times \vec{r}) dt
\end{aligned} \quad (32)$$

Here, when the rotation of the particle is considered, the rotational degree of freedom remains for the center of gravity movement. Even if the center of gravity positions coincide, there are cases where Formula (31) and Formula (32) do not coincide. Therefore, it is necessary to convert the rotational motion of the particle group 11 to the rotational motion of the coarse-view particle 21. Therefore, with respect to rotation, the angular momentum and the rotational energy are assumed to coincide before and after the coarse-view. In this case, the angular momentum is given by the following formula.

[Math 34]

$$I_{cw}\vec{\omega_{cw}} = \alpha^3 I_s \vec{\omega_s} + I_o \vec{\omega_o} \quad (33)$$

Further, the rotational kinetic energy is given by the following formula.

[Math 35]

$$\frac{1}{2}I_{cw}|\vec{\omega_{cw}}|^2 = \frac{1}{2}\alpha^3 I_s |\vec{\omega_s}|^2 + \frac{1}{2}I_o |\vec{\omega_o}|^2 \quad (34)$$

In Formula (33) and Formula (34) above, the first and second terms on the right-hand side denote the rotational motion component (Spin) and the orbital motion component (Orbit) of the particle group before being coarsely viewed, respectively. The vectors $\delta_{cw}$, $\omega_s$, and $\omega_o$ ($\omega_{cw}$, $\omega_s$, and $\omega_o$ indicated by an arrow above in Formula (33) and Formula (34)) denote the angular velocity of the coarse-view particle, the angular velocity of the rotational motion of the particle group before being coarsely viewed, and the angular velocity of the orbital motion of the particle group before being coarsely viewed, respectively. Further, $I_{cw}$, $I_s$ and $I_o$ denote the moment of inertia of the coarse-view particle, the moment of inertia of the rotational motion of the particle group before being coarsely viewed, and the moment of inertia of the orbital motion of the particle group before being coarsely viewed.

When the orbital motion component is eliminated by combining Formula (33) and Formula (34), the following Formula (35) is obtained.

[Math 36]

$$\vec{\omega_{cw}} = \frac{\alpha^2 + 1}{2\alpha^2}\vec{\omega_s} \tag{35}$$

From this, the amount of overlap in the tangential direction of the coarse-view particle can be defined as follows.

[Math 37]

$$\delta_{cw,t}\hat{t} \stackrel{def}{=} \int_{start}^{end} \vec{v_{cw,t}} + \frac{2\alpha^2}{\alpha^2+1}\vec{\omega_{cw}} \times \alpha\vec{r}dt \tag{36}$$

Under this definition, as in the vertical direction, the following Formula (37) holds.

[Math 38]

$$\delta_{w,t} + \frac{1}{2}(\alpha - 1)\delta_{p,t} = \delta_{cw,t} \tag{37}$$

Herein, Formula (33), Formula (34), and Formula (35) are used for simplification of calculation, but there are several possible types depending on the shape of the coarse-view particle. For example, an attempt to calculate the moment of inertia by considering the shape factor of the coarse-view particle in the cubic shape yields the following Formula (38) to Formula (41).

[Math 39]

$$I_{cw}\vec{\omega_{cw}} = \alpha^3 I_s\vec{\omega_s} + I_o\vec{\omega_o} \tag{38}$$

[Math 40]

$$I_c = \frac{2}{5}r^2 m\alpha^5 \tag{39}$$

[Math 41]

$$I_s = \frac{2}{5}r^2 m \tag{40}$$

[Math 42]

$$I_o = \frac{1}{3}r^2 m\alpha^3(\alpha^2 - 1) \tag{41}$$

Therefore, assuming $\omega_s = \omega_o$ with respect to angular momentum storage and vectors $\omega_s$ and $\omega_o$, Formula (42) and Formula (43) below are obtained from Formula (38).

[Math 43]

$$\vec{\omega_s} = \beta(\alpha)\vec{\omega_{cw}} \tag{42}$$

[Math 44]

$$\beta(\alpha) \stackrel{def}{=} \frac{6\alpha^2}{5\alpha^2 + 1} \tag{43}$$

Alternatively, the relationship between the vectors $\omega_s$ and the vector $\omega_{cw}$ may be determined with respect to the vectors $\omega_s$ and $\omega_o$, for example, by assuming $\omega_s = \omega_o$. These can be selected according to the phenomena to be calculated.

In this way, it is also possible to determine the amount of overlap of the particles constituting the particle group before being coarsely viewed.

(1-2) Equation of Rotational Motion

The tangential force can be calculated from the amount of overlap in the tangential direction described so far to calculate the torque. The rolling friction between each particle and between the particle and the wall surface generates a torque proportional to the product of the vertical drag on the particle and the contact radius. Since each rolling friction is generated in each particle, the rolling friction resistance across the coarse-view particle can be expressed by the following Formula (44).

In Formula (44), the vector $T_{tot\_fric}$ denotes the rolling friction resistance of the entire coarse-view particle, the vector $T_{w,fric}$ denotes the rolling friction resistance between the particle group 11 and the wall surface 12 or the external particle, and the vector $T_{p,fric}$ represents the rolling friction resistance between internal particles of particle group 11. Each vector is represented by an arrow above the letter in the formula below. Note that in the particle group 11, the vector $T_{p,fric}$ is doubled, as illustrated in Formula (44), because the opposite contact force is exerted by the action-reaction between particles.

The vectors $T_{w,fric}$ and $T_{p,fric}$ are represented by Formula (45) and Formula (46). Note that hat ω in the formula denotes a unit vector in the direction of rotation.

[Math 45]

$$\vec{T_{tot\_fric}} = \vec{T_{w,fric}} + 2\vec{T_{p,fric}} \tag{44}$$

[Math 46]

$$\vec{T_{w,fric}} = -\mu_w \alpha^2 F_w r_{w,cont}\hat{\omega} \tag{45}$$

[Math 47]

$$\vec{T_{p,fric}} = -\mu_p \alpha^2(\alpha-1)F_p r_{p,cont}\hat{\omega} \tag{46}$$

The contact radius $r_w$ and $r_p$ in Formula (45) and Formula (46) can be geometrically calculated from the amount of overlap, and the accuracy can be enhanced by using the amount of overlap calculated based on the previously described definition of the equation of motion in the tangential direction. Further, $\mu_w$ denotes the rolling friction coefficient of the particle group 11 with the wall surface 12 or with the external particle, and pp denotes the rolling friction coefficient of the internal particles of the particle group 11.

Further, the equation of motion in the rotational direction can be expressed as follows.

[Math 48]

$$I_c \frac{d\vec{\omega_c}}{dt} = \alpha^3 \vec{r} \times \overrightarrow{F_{w,t}} + \alpha^3 \vec{r} \times \overrightarrow{F_{dw,t}} + \overrightarrow{T_{w,fric}} + \overrightarrow{2T_{p,fric}} \quad (47)$$

(2) Simulation Device

Even in the simulation device of the present embodiment, the second parameter calculation unit can calculate the second parameter by using the solution of the characteristic equation using the relationship between the elastic energy of the particle group and the elastic energy of the coarse-view particle. However, when the equation of motion in the tangential direction is used, it is possible to calculate the amount of overlap by assuming that the angular momentum and rotational energy coincide before and after coarse-view. Further, in the case of the equation of motion in the rotational direction being used, when calculating the torque, the amount of overlap calculated in the case of the equation of motion in the tangential direction being used can be used.

Except for the above points, since the configuration can be the same as that of the simulation device according to the first embodiment, the description will not be repeated here.

<Simulation Method>

Even in the simulation method of the present embodiment, in the second parameter calculation process, the second parameter can be calculated by using the solution of the characteristic equation derived using the relationship between the elastic energy of the particle group before being coarsely viewed and the elastic energy of the coarse-view particle. However, when the equation of motion in the tangential direction is used, it is possible to calculate the amount of overlap by assuming that the angular momentum and rotational energy coincide before and after coarse-view. Further, in the case of the equation of motion in the rotational direction being used, when calculating the torque, the amount of overlap calculated in the case of the equation of motion in the tangential direction being used can be used.

Except for the above points, since the configuration can be the same as that of the simulation method according to the first embodiment, the description will not be repeated here.

<Program>

Even in the program according to this embodiment, the second parameter calculation unit can calculate the second parameter by using the solution of the characteristic equation using the relationship between the elastic energy of the particle group and the elastic energy of the coarse-view particle. However, when the equation of motion in the tangential direction is used, it is possible to calculate the amount of overlap by assuming that the angular momentum and rotational energy coincide before and after coarse-view. Further, in the case of the equation of motion in the rotational direction being used, when calculating the torque, the amount of overlap calculated in the case of the equation of motion in the tangential direction being used can be used.

Except for the above points, since the configuration can be the same as that of the program according to the first embodiment, the description will not be repeated here.

EMBODIMENTS

Although specific embodiments will be described below, the present invention is not limited to these embodiments.

Experimental Example 1

Comparative Example 1-1

Figure 6:
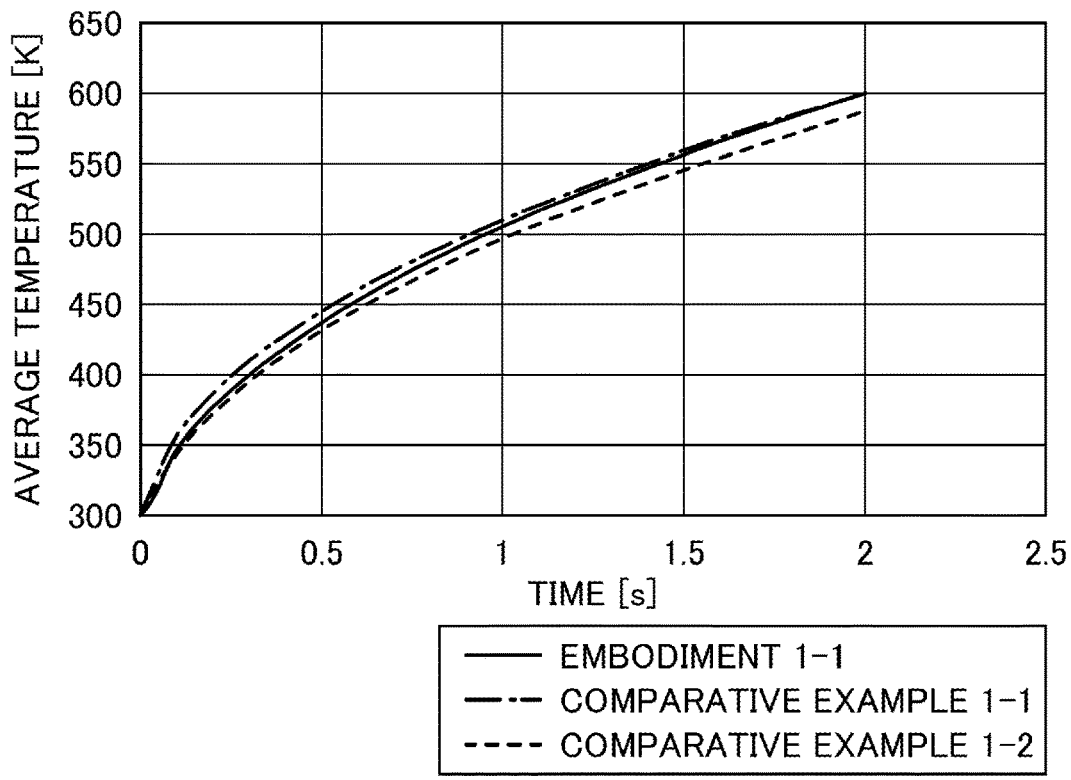
FIG. 6 is a graph illustrating a change in an average temperature of a granular material in Experimental Example 1.

The temperature change of the granular material layer filled in a rectangular container was analyzed by the discrete element method calculation when heating was performed from the bottom using the parameters illustrated in Table 1. The change in the average temperature of the granular material layer in the container obtained by the analysis is illustrated in FIG. 6. The coefficient of restitution was 0.1, the coefficient of friction was 0.7, and the coefficient of rolling friction was 0.001.

TABLE 1

|  | EMBODIMENT 1-1 | COMPARATIVE EXAMPLE 1-1 | COMPARATIVE EXAMPLE 1-2 |
| --- | --- | --- | --- |
| PARTICLE SIZE | 4 mm | 2 mm | 4 mm |
| PARTICLE-PARTICLE THERMAL CONDUCTIVITY | 1107 W/m | 1000 W/m | 1000 W/m |
| PARTICLE-WALL THERMAL CONDUCTIVITY | 1196 W/m | 1000 W/m | 1000 W/m |
| INITIAL TEMPERATURE | 300 K | 300 K | 300 K |
| YOUNG'S MODULUS |  | $2.5 \times 10^6$ Pa |  |
| POISSON'S RATIO |  | 0.25 |  |

Comparative Example 1-2

The temperature change of the granular material layer filled in the rectangular container was analyzed under the same conditions as in Comparative Example 1-1 except that the coarse-view magnification α was set at 2 and the particle group including 8 particles was made into a single coarse-view particle. Although the particle size was changed as illustrated in Table 1 because the coarse-view particle was used, the analysis was performed using the same parameters as in Comparative Example 1-1 except for the particle size. The change in the average temperature of the granular material layer in the container obtained by the analysis is illustrated in FIG. 6.

Embodiment 1-1

The temperature change of the granular material layer filled in the rectangular container was analyzed using the simulation device described above, with the coarse-view magnification α set at 2.

Specifically, the first parameter including a parameter related to the granular material to be analyzed was acquired by the first parameter acquisition unit 421 (i.e., the first parameter acquisition process S1).

In this case, the same parameters as in Comparative Example 1-2 were obtained.

Then, the second parameter calculation unit 422 calculated the second parameter, which is a parameter for the coarse-view particle (i.e., the second parameter calculation process S2).

At this time, the thermal conductivity for the coarse-view particle was calculated by Formula (26) and Formula (27) by using the parameter $K_r$, which is the solution of the characteristic equation illustrated in Formula (13) and Formula (19) above. The coefficient of restitution, the coefficient of friction, and the coefficient of rolling friction were calculated by using the characteristic equation. As described above, depending on the model applied to the calculation, these coefficients are adjustable and can be calculated and converted by using the characteristic equation as described above. The calculated parameter $K_r$ is illustrated in Table 2.

TABLE 2

| | | Kr |
|---|---|---|
| VERTICAL DIRECTION | PARTICLE-PARTICLE | 0.4805 |
| | PARTICLE-WALL | 0.6057 |
| TANGENTIAL DIRECTION | PARTICLE-PARTICLE | 0.6135 |
| | PARTICLE-WALL | 0.7159 |

The obtained, calculated first parameter and second parameter are illustrated in Table 1. Then, based on the parameters illustrated in Table 1, the behavior of the coarse-view particle, specifically the temperature change, was analyzed in the coarse-view particle behavior analysis unit 423 (i.e., the coarse-view particle behavior analysis process S3). The results are illustrated in FIG. 6.

According to the results illustrated in FIG. 6, the result of Embodiment 1-1 is almost identical to the result of Comparative Example 1-1, which did not perform coarse-view, and it can be checked that the parameters of the coarse-view particle were appropriately selected, set, and analyzed.

In Embodiment 1-1, the number of particles is ⅛ times larger than in Comparative Example 1-1 because of the coarse-view, and the amount of calculation can be reduced compared to Comparative Example 1-1.

Experimental Example 2

Comparative Example 2-1

Figure 13:
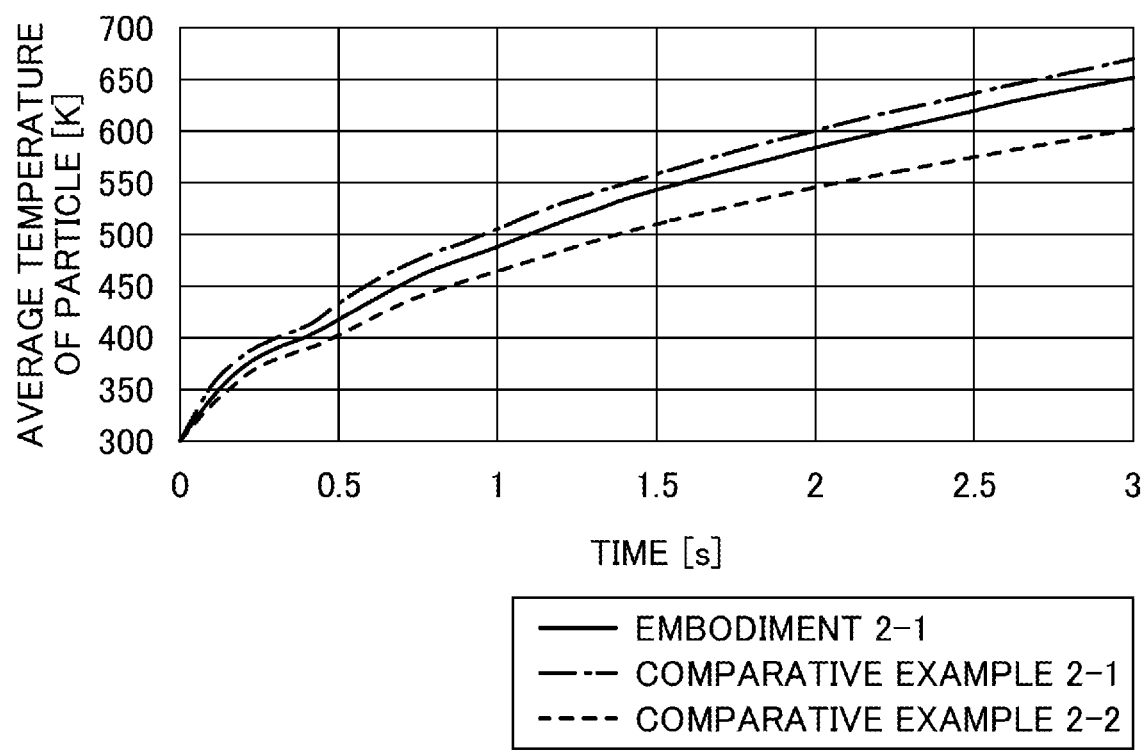
FIG. 13 is a graph illustrating a change in an average temperature of a granular material in Experimental Example 2.

The behavior of the granular material in the kiln, which is a rotating body, was analyzed by the discrete element method calculation using the parameters illustrated in Table 3. The coefficient of restitution was 0.75, the coefficient of friction was 0.3, and the coefficient of rolling friction was 0.5. The movement of granular material in the kiln obtained by the analysis is illustrated in FIG. 8A to 8D, the temperature distribution of the granular material in the kiln obtained by the analysis is illustrated in FIG. 11A to 11C, and the average temperature of the granular material (particles) in the kiln obtained by the analysis is illustrated in FIG. 13.

Figure 8A:
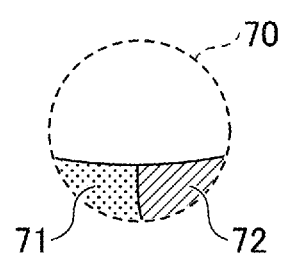
FIG. 8A illustrates a state of mixing of a granular material in the kiln in Comparative Example 2-1.
Figure 8B:
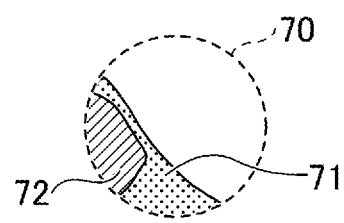
FIG. 8B illustrates a state of mixing of the granular material in the kiln in Comparative Example 2-1.
Figure 8C:
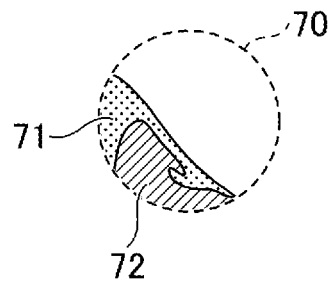
FIG. 8C illustrates a state of mixing of the granular material in the kiln in Comparative Example 2-1.
Figure 8D:
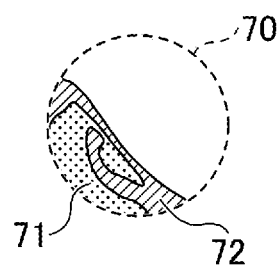
FIG. 8D illustrates a state of mixing of the granular material in the kiln in Comparative Example 2-1.

FIG. 8A illustrates the state before a kiln 70 begins to rotate, with the grouped first granular material group 71 and the second granular material group 72 half each. FIGS. 8B, 8C, and 8D illustrate the state of the kiln at 2 seconds, 4 seconds, and 6 seconds after the start of the rotation, respectively, and illustrate the state in which the first granular material group 71 and the second granular material group 72 are mixed.

Figure 11A:
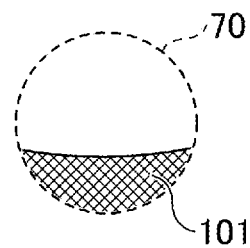
FIG. 11A illustrates a temperature distribution of a granular material in the kiln in Comparative Example 2-1.
Figure 11B:
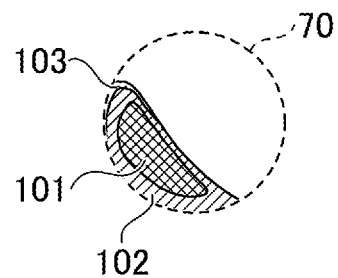
FIG. 11B illustrates a temperature distribution of the granular material in the kiln in Comparative Example 2-1.
Figure 11C:
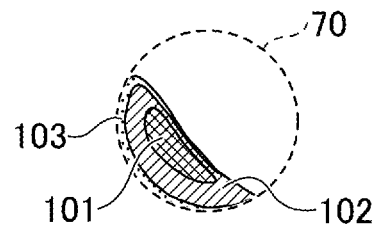
FIG. 11C illustrates a temperature distribution of the granular material in the kiln in Comparative Example 2-1.

FIG. 11A illustrates the state before the kiln 70 begins to rotate, it can be checked that the temperature is within the first temperature region 101 and is uniform. FIGS. 11B and 11C illustrate the state of the kiln 3 seconds after the start of rotation and 6 seconds after the start of the rotation, respectively. Since the kiln 70 is heated from the outer wall side of the kiln 70, it can be confirmed that the first temperature region 101, the second temperature region 102, and the third temperature region 103 are distributed in order from the center side of the granular material. The temperature increases in the order of the first temperature region 101, the second temperature region 102, and the third temperature region 103.

TABLE 3

| | EMBODIMENT 2-1 | COMPARATIVE EXAMPLE 2-1 | COMPARATIVE EXAMPLE 2-2 |
|---|---|---|---|
| PARTICLE SIZE | 8 mm | 2 mm | 8 mm |
| PARTICLE-PARTICLE THERMAL CONDUCTIVITY | 1176 W/m | 1000 W/m | 1000 W/m |
| PARTICLE-WALL THERMAL CONDUCTIVITY | 1350 W/m | 1000 W/m | 1000 W/m |
| WALL TEMPERATURE | | 1000 K | |
| NUMBER OF ROTATIONS | | 10 rpm | |
| YOUNG'S MODULUS | | $2.5 \times 10^6$ Pa | |
| POISSON'S RATIO | | 0.25 | |

Comparative Example 2-2

The behavior of the granular material in the kiln, which is a rotating body, was analyzed under the same conditions as in Comparative Example 2-1 except that the coarse-view magnification α was 4 and the particle group including 64 particles was made into a single coarse-view particle. As illustrated in Table 3, the analysis was performed using the same parameters as in Comparative Example 2-1 except for the particle size. The movement of granular material in the kiln determined by the analysis is illustrated in FIG. 9A to 9D, the temperature distribution of granular material in the kiln determined by the analysis is illustrated in FIG. 12A to 12C, and the average temperature of granular material in the kiln determined by the analysis is illustrated in FIG. 13.

Figure 9A:
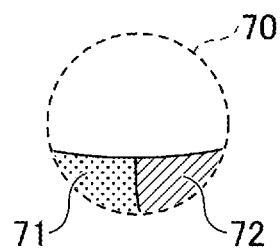
FIG. 9A illustrates a state of mixing of a granular material in the kiln in Comparative Example 2-2.
Figure 9B:
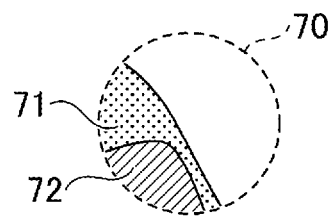
FIG. 9B illustrates a state of mixing of the granular material in the kiln in Comparative Example 2-2.
Figure 9C:
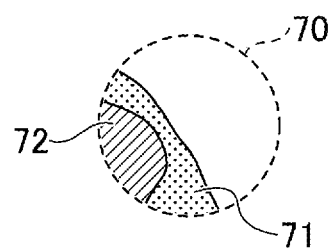
FIG. 9C illustrates a state of mixing of the granular material in the kiln in Comparative Example 2-2.
Figure 9D:
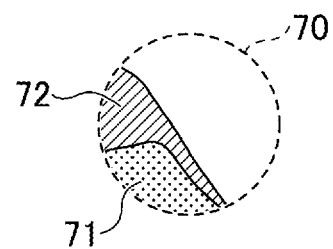
FIG. 9D illustrates a state of mixing of the granular material in the kiln in Comparative Example 2-2.

FIG. 9A illustrates the state before the kiln 70 begins to rotate, with the grouped first granular material group 71 and the second granular material group 72 half each. FIGS. 9B, 9C, and 9D illustrate the state of the kiln at 2 seconds, 4 seconds, and 6 seconds after the start of the rotation, respectively, and illustrate the state in which the first granular material group 71 and the second granular material group 72 are mixed.

Figure 12A:
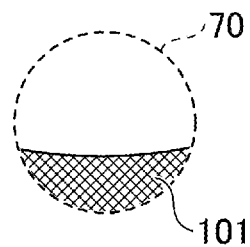
FIG. 12A illustrates a temperature distribution of a granular material in the kiln in Comparative Example 2-2.
Figure 12B:
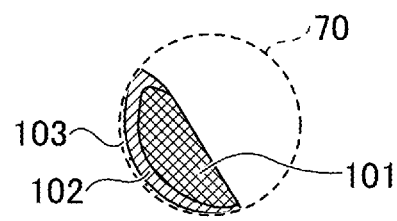
FIG. 12B illustrates a temperature distribution of the granular material in the kiln in Comparative Example 2-2.
Figure 12C:
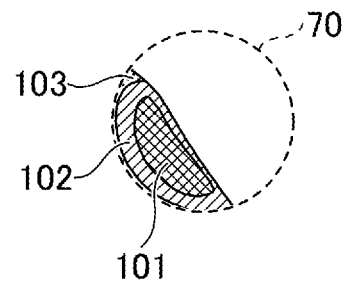
FIG. 12C illustrates a temperature distribution of the granular material in the kiln in Comparative Example 2-2.

FIG. 12A illustrates the state before the kiln 70 begins to rotate, it can be checked that the temperature is within the first temperature region 101 and is uniform. FIGS. 12B and 12C illustrate the state of the kiln 3 seconds after the start of rotation and 6 seconds after the start of the rotation, respectively. Since the kiln 70 is heated from the outer wall side of the kiln 70, it can be confirmed that the first temperature region 101, the second temperature region 102, and the third temperature region 103 are distributed in order from the center side of the granular material. The temperature increases in the order of the first temperature region 101, the second temperature region 102, and the third temperature region 103.

Embodiment 2-1

The behavior of the granular material in the kiln, which is a rotating body, was analyzed using the simulation device described above, with the coarse-view magnification α set at 4.

Specifically, the first parameter including a parameter related to the granular material to be analyzed was acquired by the first parameter acquisition unit 421 (i.e., the first parameter acquisition process S1).

In this case, the same parameters as in Comparative Example 2-2 were obtained.

Then, the second parameter calculation unit 422 calculated the second parameter, which is a parameter for the coarse-view particle (i.e., the second parameter calculation process S2).

At this time, the thermal conductivity for the coarse-view particle was calculated by Formula (26) and Formula (27) by using the parameter $K_r$, which is the solution of the characteristic equation illustrated in Formula (13) and Formula (19) above. The coefficient of restitution, the coefficient of friction, and the coefficient of rolling friction were calculated by using the characteristic equation. The calculated parameter $K_r$ is illustrated in Table 4.

TABLE 4

| | | Kr |
|---|---|---|
| VERTICAL DIRECTION | PARTICLE-PARTICLE | 0.2036 |
| | PARTICLE-WALL | 0.3084 |
| TANGENTIAL DIRECTION | PARTICLE-PARTICLE | 0.3460 |
| | PARTICLE-WALL | 0.4565 |

The obtained, calculated first parameter and second parameter are illustrated in Table 3. Then, based on the parameters illustrated in Table 3, the behavior of the coarse-view particle, specifically the movement in the kiln or the temperature change, was analyzed in the coarse-view particle behavior analysis unit 423 (i.e., the coarse-view particle behavior analysis step S3). The movement of the granular material in the kiln obtained by analysis is illustrated in FIG. 7A to 7D, the temperature distribution of granular material in the kiln obtained by analysis is illustrated in FIG. 10A to 10C, and the average temperature of granular material in the kiln obtained by analysis is illustrated in FIG. 13.

Figure 7A:
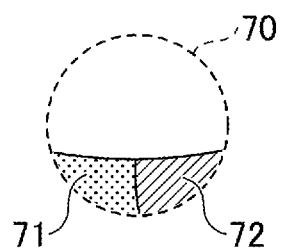
FIG. 7A illustrates a state of mixing of a granular material in a kiln in Embodiment 2-1.
Figure 7B:
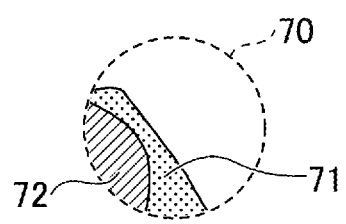
FIG. 7B illustrates a state of mixing of the granular material in a kiln in Embodiment 2-1.
Figure 7C:
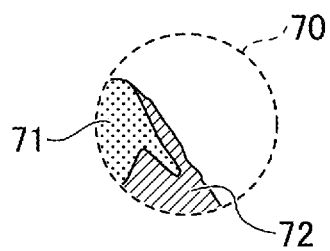
FIG. 7C illustrates a state of mixing of the granular material in the kiln in Embodiment 2-1.
Figure 7D:
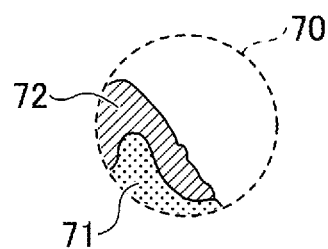
FIG. 7D illustrates a state of mixing of the granular material in the kiln in Embodiment 2-1.

FIG. 7A illustrates the state before the kiln 70 begins to rotate, with the grouped first granular material group 71 and the second granular material group 72 half each. FIGS. 7B, 7C, and 7D illustrate the state of the kiln at 2 seconds, 4 seconds, and 6 seconds after the start of the rotation, respectively, and illustrate the state in which the first granular material group 71 and the second granular material group 72 are mixed.

Figure 10A:
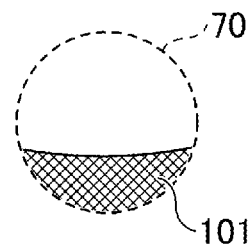
FIG. 10A illustrates a temperature distribution of a granular material in the kiln in Embodiment 2-1.

FIG. 10A illustrates the state before the kiln 70 begins to rotate, it can be checked that the temperature is within the first temperature region 101 and is uniform. FIGS. 10B and 10C illustrate the state of the kiln 3 seconds after the start of rotation and 6 seconds after the start of the rotation, respectively. Since the kiln 70 is heated from the outer wall side of the kiln 70, it can be confirmed that the first temperature region 101, the second temperature region 102, and the third temperature region 103 are distributed in order from the center side of the granular material. The temperature increases in the order of the first temperature region 101, the second temperature region 102, and the third temperature region 103.

Figure 10B:
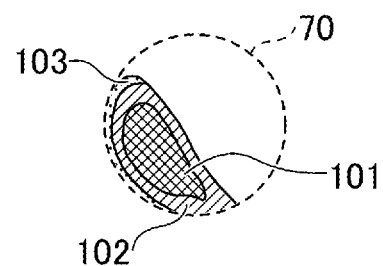
FIG. 10B illustrates a temperature distribution of the granular material in the kiln in Embodiment 2-1.
Figure 10C:
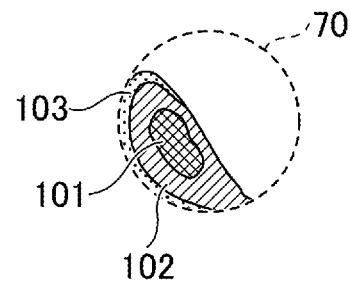
FIG. 10C illustrates a temperature distribution of the granular material in the kiln in Embodiment 2-1.

As is clear from the comparison of FIG. 7A to 7D with FIG. 8A to 8D and from the comparison of FIG. 10A to 10C with FIG. 11A to 11C, the result of Embodiment 2-1 is almost identical to the result of Comparative Example 2-1, which did not perform coarse-view, and it can be checked that the parameters of the coarse-view particle were appropriately selected, set, and analyzed.

In FIG. 13, it can be checked that Embodiment 2-1 and Comparative Example 2-1 had similar tendencies such as having an inflection point.

Further, in Embodiment 2-1, the number of particles is 1/64 times larger than in Comparative Example 2-1 because of the coarse-view, and the amount of calculation can be reduced compared to Comparative Example 2-1.

As described above, a simulation device, a simulation method, and a program has been described with reference to the above-described embodiment and example, but the present invention is not limited to the aforementioned embodiment and example. Various modifications and variations are possible within the scope of the subject matter of the invention as defined in the claims.

What is claimed is:

1. A simulation device for analyzing behavior of a granular material that includes a plurality of particles, the simulation device comprising:
a processor; and
a memory storing program instructions that cause the processor to:
acquire a first parameter including a parameter relating to the granular material,
obtain a second parameter relating to a single particle model, the single particle model being a conceptual representation in which the plurality of particles arranged in a cube are regarded as a single particle,
simulate a behavior of the single particle model based on the first parameter and the second parameter to produce a simulation result of the behavior of the single particle model,
analyze the behavior of the granular material in a reaction furnace using the simulation result of the behavior of the single particle model to produce an analysis result of the behavior of the granular material, and
supply, based on the analysis result of the behavior of the granular material, the granular material from a granular supply device to the reaction furnace,
wherein, in the obtaining the second parameter, the program instructions stored in the memory further cause the processor to:
calculate a first elastic energy of a particle group from forces exerted on the plurality of particles when the particle group collides with a certain surface, the particle group being the plurality of particles arranged in the cube,
calculate a second elastic energy of the single particle model from a force exerted on the single particle model when the single particle model collides with the certain surface,
derive an equation that demonstrates an equivalence of the calculated first and second elastic energies,
establish a characteristic equation for the second parameter from the derived equation based on an assumption that a center of gravity of the particle group coincides with that of the single particle model, and
obtain the second parameter by solving the characteristic equation.

2. The simulation device according to claim 1, wherein the second parameter includes a thermal conductivity of the single particle model, and the processor calculates the thermal conductivity by using the solution of the characteristic equation.

3. The simulation device according to claim 1, wherein the behavior of the granular material in a rotating body of the reaction furnace is analyzed.

4. A simulation method of analyzing behavior of a granular material that includes a plurality of particles, the simulation method comprising steps:
- acquiring a first parameter including a parameter relating to the granular material,
- obtaining a second parameter relating to a single particle model, the single particle model being a conceptual representation in which the plurality of particles arranged in a cube are regarded as a single particle,
- simulating a behavior of the single particle model based on the first parameter and the second parameter to produce a simulation result of the behavior of the single particle model,
- analyzing the behavior of the granular material in a reaction furnace using the simulation result of the behavior of the single particle model to produce an analysis result of the behavior of the granular material, and
- supplying, based on the analysis result of the behavior of the granular material, the granular material from a granular supply device to the reaction furnace,
- wherein the obtaining step comprises:
- calculating a first elastic energy of a particle group from forces exerted on the plurality of particles when the particle group collides with a certain surface, the particle group being the plurality of particles arranged in the cube,
- calculating a second elastic energy of the single particle model from a force exerted on the single particle model when the single particle model collides with the certain surface,
- deriving an equation that demonstrates an equivalence of the calculated first and second elastic energies,
- establishing a characteristic equation for the second parameter from the derived equation based on an assumption that a center of gravity of the particle group coincides with that of the single particle model, and
- obtaining the second parameter by solving the characteristic equation.

5. The simulation method according to claim 4, wherein the second parameter includes a thermal conductivity of the single particle model, and the thermal conductivity is calculated by using the solution of the characteristic equation.

6. A simulation device for analyzing behavior of a granular material that includes a plurality of particles, the simulation device comprising:
- a processor; and
- a memory storing program instructions that cause the processor to:
  - acquire a first parameter including a parameter relating to the granular material,
  - obtain a second parameter relating to a single particle model, the single particle model being a conceptual representation in which the plurality of particles arranged in a cube are regarded as a single particle,
  - simulate a behavior of the single particle model based on the first parameter and the second parameter to produce a simulation result of the behavior of the single particle model,
  - analyze the behavior of the granular material in a reaction furnace using the simulation result of the behavior of the single particle model to produce an analysis result of the behavior of the granular material, and
  - supply, based on the analysis result of the behavior of the granular material, the granular material from a granular supply device to the reaction furnace,
- wherein, in the obtaining the second parameter, the program instructions stored in the memory further cause the processor to:
- calculate a first elastic energy of a particle group from forces exerted on the plurality of particles when the particle group collides with a certain surface, the particle group being the plurality of particles arranged in the cube,
- calculate a second elastic energy of the single particle model from a force exerted on the single particle model when the single particle model collides with the certain surface,
- derive an equation that demonstrates an equivalence of the calculated first and second elastic energies,
- establish a characteristic equation for the second parameter from the derived equation based on an assumption that a center of gravity, an angular momentum, and a rotational energy of the particle group and the single particle model are coincide, and
- obtain the second parameter by solving the characteristic equation.

7. A simulation method of analyzing behavior of a granular material that includes a plurality of particles, the simulation method comprising:
- acquiring a first parameter including a parameter relating to the granular material,
- obtaining a second parameter relating to a single particle model, the single particle model being a conceptual representation in which the plurality of particles arranged in a cube are regarded as a single particle,
- simulating a behavior of the single particle model based on the first parameter and the second parameter to produce a simulation result of the behavior of the single particle model,
- analyzing the behavior of the granular material in a reaction furnace using the simulation result of the behavior of the single particle model to produce an analysis result of the behavior of the granular material, and
- supplying, based on the analysis result of the behavior of the granular material, the granular material from a granular supply device to the reaction furnace,
- wherein the obtaining step comprises:
- calculating a first elastic energy of a particle group from forces exerted on the plurality of particles when the particle group collides with a certain surface, the particle group being the plurality of particles arranged in the cube,
- calculating a second elastic energy of the single particle model from a force exerted on the single particle model when the single particle model collides with the certain surface,
- deriving an equation that demonstrates an equivalence of the calculated first and second elastic energies,
- establishing a characteristic equation for the second parameter from the derived equation based on an assumption that a center of gravity, an angular momentum, and a rotational energy of the particle group and the single particle model are coincide, and
- obtaining the second parameter by solving the characteristic equation.

* * * * *